(12) United States Patent
Salagnad et al.

(10) Patent No.: US 6,902,927 B2
(45) Date of Patent: Jun. 7, 2005

(54) ENZYMATIC PROCESS FOR THE ENANTIOMERIC RESOLUTION OF AMINO ACIDS

(75) Inventors: Christophe Salagnad, Oberursel (DE); Claude Gobert, L'Hay les Roses (FR); Marie-Odile Dury, Ablon (FR)

(73) Assignee: Aventis Pharma S.A., Antony Cedex (FR)

( * ) Notice: Subject to any disclaimer, the term of this patent is extended or adjusted under 35 U.S.C. 154(b) by 451 days.

(21) Appl. No.: 10/232,674

(22) Filed: Sep. 3, 2002

(65) Prior Publication Data

US 2003/0087399 A1 May 8, 2003

Related U.S. Application Data

(60) Provisional application No. 60/331,613, filed on Nov. 20, 2001.

(30) Foreign Application Priority Data

Sep. 4, 2001 (FR) .............................. 01 11431

(51) Int. Cl.$^7$ .......................... C12P 13/04; C07C 7/148
(52) U.S. Cl. ....................... 435/280; 435/106
(58) Field of Search ................. 435/280, 106

(56) References Cited

FOREIGN PATENT DOCUMENTS

WO     WO 98/50575     11/1998

OTHER PUBLICATIONS

Raimondi et al. "Kinetic resolutions of racemic amines and alcohols catalyzed by an industrial glutaryl–7–aminocephalosporanic acylase with unexpected broad substrate specificity," Tetrahedron: Assymetry (2003) 14: 1091–1094.*

Raimondi et al. "Glutaryl acylases : One–reaction enzymes or versatile enantioselective biocatalysts?" Adv. Synth. Cata. (2003) 345: 783–789.*

Shibuya et al., "Isolation and Properties of 7β–(4–Carboxybutanamido)cephalosporanic Acid Acylase–producing Bacteria," Agric. Biol. Chem., 45(7): 561–1567 (1981).

Soloshonok et al., "Biocatalytic Approach to Enantiomerically Pure β–Amino Acids," Tetrahedron: Asymmetry, 6(7): 1601–1610 (1995).

Topgi et al., "Use of Enzyme Penicillin Acylase in Selective Amidation/Amide Hydrolysis to Resolve Ethyl 3–amino–4–pentynoate Isomers," Bioorganic & Medicinal Chemistry 7:2221–2229 (1999).

* cited by examiner

*Primary Examiner*—Jean C. Witz
*Assistant Examiner*—Susan Hanley
(74) *Attorney, Agent, or Firm*—Balaram Gupta

(57) ABSTRACT

An enzymatic process permitting the enantiomeric resolution of amino acids is provided. More specifically, this process for separating the enantiomers of an amino acid comprises treating a racemic mixture of the amino acid with glutaric anhydride and then with the enzyme glutaryl-7-ACA acylase so as to recover one of the enantiomers of the amino acid, the other enantiomer remaining in the form of the corresponding glutarylamide derivative.

20 Claims, 2 Drawing Sheets

(S) enantiomer
(IV)

(S) enantiomer
(V)

or else:

(R) enantiomer
(IV')

(R) enantiomer
(V')

ENZYMATIC PROCESS FOR THE ENANTIOMERIC RESOLUTION OF AMINO ACIDS

The present application claims priority under 35 U.S.C. § 119(e) of U.S. Provisional Application No. 60/331,613, filed Nov. 20, 2001, the disclosure of which is expressly incorporated by reference herein. The present application also claims priority under 35 U.S.C. § 119 of French Application No. 01/11431, filed Sep. 4, 2001, the disclosure of which is expressly incorporated by reference herein.

The present invention relates to a novel enzymatic process permitting the enantiomeric resolution of amino acids in the form of the racemic mixture.

Amino acids are often used in all kinds of industries either, for example, as biologically active compounds or as synthesis intermediates for the preparation of compounds for pharmaceutical, chemical or agricultural purposes in particular. Accordingly, it became evident very quickly that it was often necessary to be able to have available one or the other optically active enantiomer of these amino acids.

Numerous routes for separating the enantiomers of prochiral amino acids were therefore developed. In particular, enzymatic processes permitting their enantiomeric resolution were found to be an advantageous alternative to the asymmetric synthesis approaches.

Thus it was that Soloshonok et al. (*Tetrahedron: Assymetry*, Vol. 6(7), 1995, pp. 1601–1610) employed an enzymatic process for enantiomeric resolution of β-amino acids in accordance with the following reaction scheme:

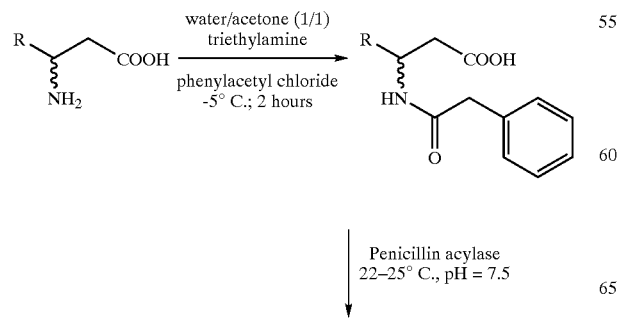

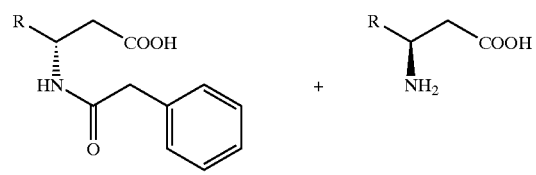

Similarly, Topgi et al. (*Bioorg. & Med. Chem.* 1999, Vol. 7, pp. 2221–2229) elaborated a process for resolving the (R) and (S) enantiomers of ethyl 3-amino-4-pentynoate in enantiomerically pure form in accordance with one of the following reaction schemes:

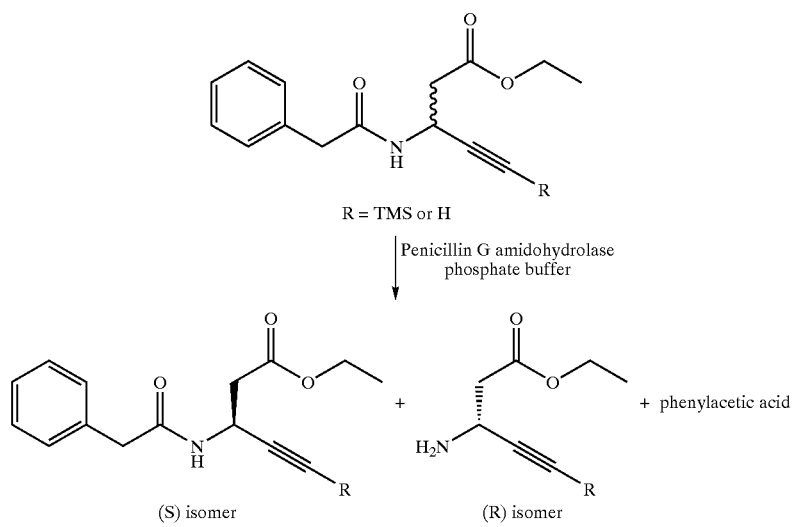

the initial phenylacetamide being obtained by acylating the corresponding amine by reaction with phenylacetic acid, or else:

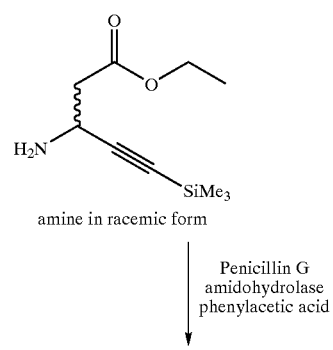

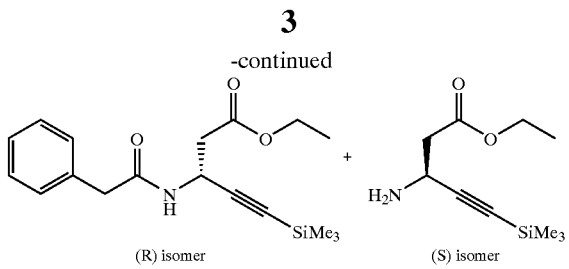

(R) isomer     (S) isomer

The patent application WO 98/50575 describes in more general terms a method of preparing a chiral β-amino acid, which comprises contacting a racemic mixture of the said amino acid with an acyl donor and the enzyme Penicillin G acylase (or amidohydrolase) under conditions appropriate for stereoselectively acylating one of the enantiomers of the racemic mixture of the β-amino acid to its corresponding N-acylated derivative, the opposite enantiomer of the β-amino acid being obtained in an enantiomerically enriched form, in accordance with the following reaction scheme:

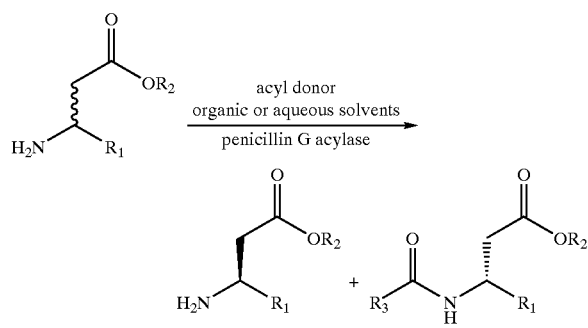

the "acyl donor" in question being of general formula:

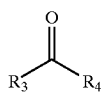

in which $R_3$ is selected from phenyl, phenoxy, amino, various derivatives of phenyl, and pyridyl, and $R_4$ is selected from the substituents hydroxyl, alkoxy, alkyl, alkenyl, alkynyl, haloalkyl, aryl, arylalkyl, from sugars or steroids.

The patent application WO 98/50575 also describes another alternative for preparing a chiral β-amino acid, which comprises contacting an amide in racemic form with the enzyme Penicillin G acylase under conditions appropriate for selectively deacylating one of the enantiomers of the amide in racemic form to its corresponding β-amino acid, the opposite enantiomer of the amide being obtained in an enantiomerically enriched form, in accordance with the following reaction scheme:

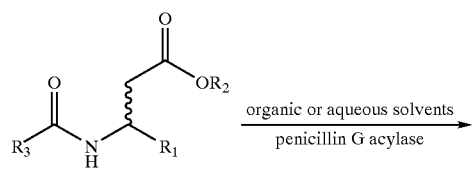

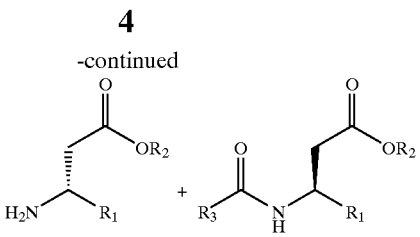

The processes discussed above, however, exhibit the major drawback of proceeding, prior to or simultaneously with the enzymatic step as such, via an intermediate amide whose formula may be summarized as follows:

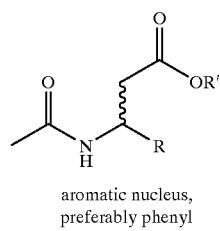

aromatic nucleus, preferably phenyl

Such an amide is insoluble in an aqueous medium owing to the present of the aromatic nucleus, which has drawbacks. For example, it is known that certain enzymes are soluble in an aqueous medium and are often sensitive to the presence of organic solvents. However, in order to be able to optimize the yield of the enzymatic reaction, it is important to have good solubility of the substrate relative to the enzyme, in order that they may be in intimate contact.

It is primarily this drawback which the present invention proposes to resolve. In effect, the present invention relates, according to a first aspect, to a novel process for separating enantiomers of an amino acid, which consists in treating a racemic mixture of the said amino acid with glutaric anhydride and then with the enzyme glutaryl-7-ACA acylase so as to recover one of the enantiomers of the said amino acid, the other enantiomer remaining in the form of the corresponding glutarylamide derivative.

This process is particularly advantageous because the use of glutaric anhydride makes it possible to proceed intermediately via a glutarylamide derivative corresponding to the initial amino acid, the glutaryl function conferring on the molecule its solubility in an aqueous medium. Consequently, the process of the present invention may be employed under gentle reaction conditions and in an aqueous medium; that is, in particular, without the use of an organic cosolvent.

The process of the present invention also possesses the advantage of applying comprehensively to all forms of amino acids (α, β, γ, etc). In the context of the present invention, the generic term "amino acid" embraces not only the amino acids as such (that is, the compounds having an amino function and an acid function —COOH) but also the corresponding ester derivatives (that is, the compounds for which the acid function is replaced by an ester function COOR). Preferentially, the process of the invention applies more specifically to the amino acids of general formula (I):

(I)

in which n is an integer selected from 0, 1, 2, 3, 4, 5 or 6,

R represents a hydrogen atom or else an alkyl, alkene, alkyne, cycloalkyl, aryl radical, a condensed polycyclic hydrocarbon, or a heterocycle, all of these radicals being optionally substituted, and R' represents an alkyl, alkene, alkyne, cycloalkyl, aryl radical, a condensed polycyclic hydrocarbon, a heterocycle, or else an oxy, thio, sulphoxide or sulphonyl radical substituted by an alkyl, aryl, cycloalkyl group or a heterocycle, all of these radicals, moreover, being optionally substituted.

Figure 1:
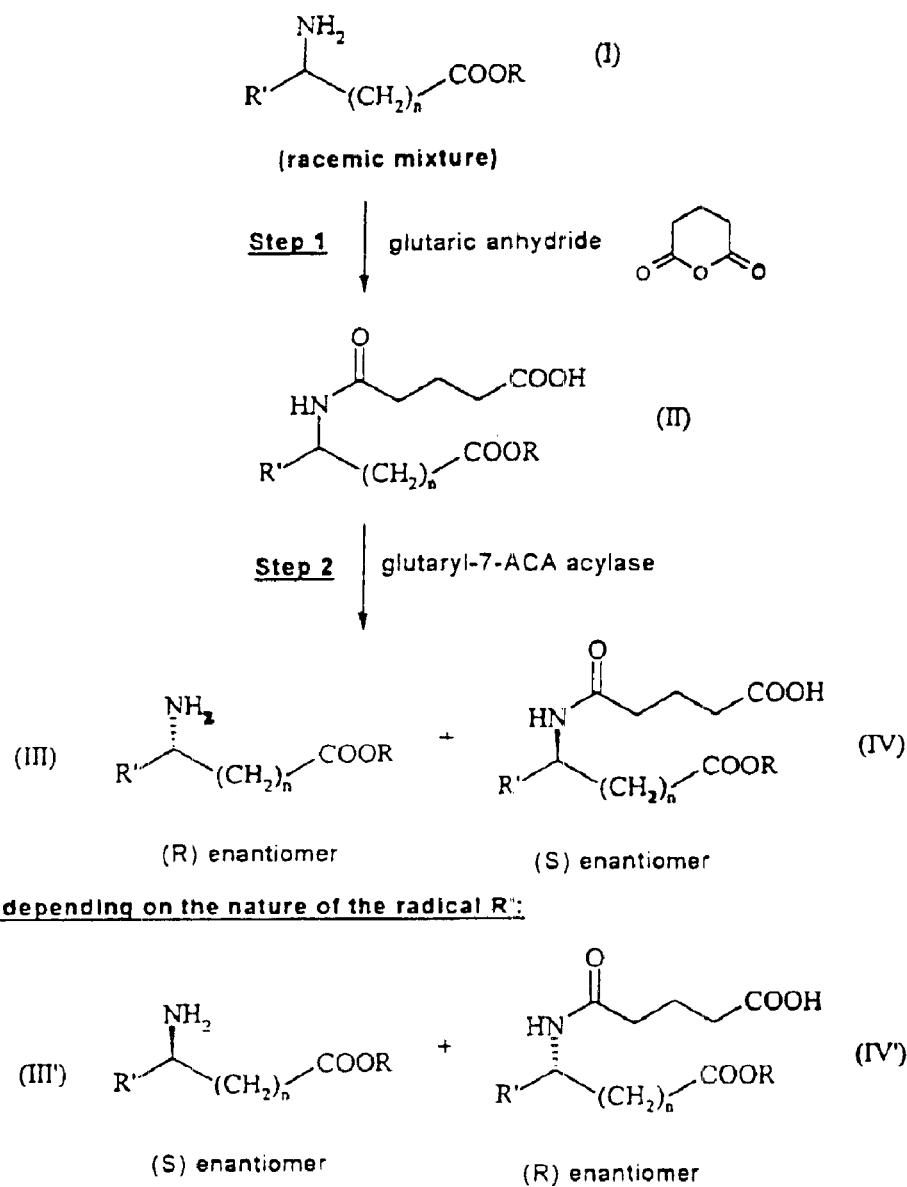
FIG. 1: Schematic representation of the $1^{st}$ step of treatment of an amino acid of general formula (I) according to the present invention with glutaric anhydride and of the $2^{nd}$ step of treatment with the enzyme glutaryl-7-ACA acylase. The configuration of each of the products obtained, namely the amino acid on the one hand and the glutarylamide derivative on the other hand, depends on the nature of the radical R'.

In the case where the amino acids are of general formula (I), the process of the present invention may be represented by the reaction scheme of FIG. 1. This scheme represents a first step of treatment with glutaric anhydride and a second step of treatment with the enzyme glutaryl-7-ACA acylase. The configuration of each of the products obtained, namely the amino acid on the one hand and the glutarylamide derivative on the other hand, depends on the nature of the radical R'.

In the context of the present invention, the alkyl, alkene and alkyne radicals contain generally between 1 and 30 carbon atoms in a straight or branched chain, without this being in any way limitative. This also applies in the cases where these radicals are substituents of other radicals. Preferably, these radicals contain between 1 and 20 carbon atoms in a straight or branched chain and, more preferably still, between 1 and 10 carbon atoms in a straight or branched chain. The alkyl radicals may be selected, for example, from: methyl, ethyl, n-propyl, n-butyl, n-pentyl, n-hexyl, n-heptyl, n-octyl, n-nonyl, n-decyl, n-undecyl, n-dodecyl, n-tridecyl, n-pentadecyl, n-hexadecyl, n-heptadecyl, n-octadecyl, isopropyl, isobutyl, isopentyl, isohexyl, 3-methylpentyl, neopentyl, neohexyl, 2,3,5-trimethylhexyl, sec-butyl, tert-butyl, tert-pentyl. Preferred alkyl radicals are, for example, methyl, ethyl, n-propyl, isopropyl, n-butyl, isobutyl, sec-butyl, tert-butyl, n-pentyl, isopentyl, n-hexyl and isohexyl. The alkene radicals may be selected, for example, from vinyl, 1-propenyl, allyl, butenyl, 2-methyl-1-propenyl, 2-methyl-2-propenyl or 3-methyl-2-butenyl. The alkyne radicals may be selected, for example, from ethynyl, 1-propynyl or propargyl.

In the context of the present invention, the cycloalkyl radicals generally contain between 3 and 12 carbon atoms. They are preferably selected from cyclopropyl, cyclobutyl, cyclopentyl, cyclohexyl, cycloheptyl, cyclooctyl, cyclononyl, cyclodecyl, cycloundecyl and cyclododecyl. According to another aspect of the present invention, the cycloalkyls may be polycyclic. Preferably, these radicals are selected from bicycloalkyls or tricycloalkyls.

According to the present invention, the term "aryl" radical refers to monovalent aromatic hydrocarbon radicals. Among the aryls, optionally substituted phenyl is preferred.

In the context of the present invention, the term condensed polycyclic hydrocarbon refers to radicals selected preferably from pentalene, indene, naphthalene, azulene, heptalene, biphenylene, as-indacene, s-indacene, acenaphthylene, fluorene, phenalene, phenanthrene, anthracene, fluoranthene, acephenanthrylene, aceanthrylene, triphenylene, pyrene, chrysene, naphthacene, pleiadene, picene, perylene, pentaphene, pentacene, tetraphenylene, hexaphene, hexacene, rubicene, coronene, trinaphthylene, heptaphene, heptacene, pyranthrene or ovalene.

In the context of the present invention, the term "heterocycle" denotes monocyclic or fused polycyclic compounds which contain one or more heteroatoms, each ring being formed of 3 to 10 members. The heterocycles according to the present invention preferably contain between 1 and 3 heteroatoms selected from oxygen, sulphur and nitrogen in a ring formed of 3 to 10 members. The heterocycles of the present invention are selected preferably from thiophene, benzo[b]thiophene, naphtho[2,3-b]thiophene, thianthrene, furan, 2H-pyran, isobenzofuran, 2H-chromene, xanthene, phenoxathiine, 2H-pyrrole, pyrrole, imidazole, pyrazole, pyridine, pyrazine, pyrimidine, pyridazine, indolizine, isoindole, 3H-indole, indole, 1H-indazole, purine, 4H-quinolizine, isoquinoline, quinoline, phthalazine, 1,8-naphthyridine, quinoxaline, quinazoline, cinnoline, pteridine, 4a H-carbazole, carbazole, β-carboline, phenanthridine, acridine, perimidine, 1,7-phenanthroline, phenazine, phenarsazine, isothiazole, phenothiazine, isoxazole, furazan, phenoxazine, isochromane, pyrrolidine, Δ2-pyrroline, imidazolidine, Δ2-imidazoline, pyrazolidine, Δ3-pyrazoline, piperidine, piperazine, indoline, isoindoline, quinuclidine and morpholine.

In the context of the present invention, when the various radicals as defined above are substituted, the said substituent or substituents are selected in general from halogen atoms, aryl, heterocycle, hydroxyl, alkoxy, aryloxy, thiol, alkylthio, arylthio, alkyl sulphoxide, aryl sulphoxide, alkylsulphonyl, arylsulphonyl, cyano, nitro, sulphonamide, alkylsulphonamide and arylsulphonamide groups, depending on the nature of the radical. Preferably, the various radicals as defined above are substituted 1, 2 or 3 times. According to a preferred aspect, the halogen atoms are selected from chlorine, fluorine, bromine and iodine. Where the alkyl radicals are substituted by halogen atoms, the atoms in question are preferably fluorine atoms. The number of fluorine substituents is preferably 1, 2, 3, 4, 5, 6 or 7. For example, the group in question may be a trifluoromethyl group.

The amino acids of the present invention are preferably selected from the compounds of general formula (I) in which n is an integer selected from 0, 1, 2 or 3, R represents a hydrogen atom or else an alkyl or aryl radical and R' is as defined above.

More preferably still, the amino acids of the present invention are selected from the compounds of general formula (I) in which n is an integer equal to 0, 1 or 2, R represents a hydrogen atom or else an alkyl function and R' is selected from optionally substituted heterocycles or aryls. In the latter case, the aryl and/or heterocycle radicals are preferably substituted 1, 2 or 3 times.

The enzyme glutaryl-7-ACA acylase has been used as a catalyst in numerous industrial processes, particularly for the hydrolysis of β-lactams such as N-glutaryl-7-aminoacetoxycephalosporinic acid. It may be derived from numerous microorganisms, for example of the genus *Acinetobacter, Arthrobacter, Bacillus, Pseudomonas, Stenotrophomonas* or else *Xanthomonas*, in accordance with the techniques which are well known to the person skilled in the art, an enzyme specialist. The enzyme glutaryl-7-ACA acylase may also be obtained commercially, for example, from Roche Diagnostic GmbH (Roche Molecular Biochemicals, Standhofer Strasse 116, D-68305 Mannheim) or else from Recordati S.p.A. (Stabilimento di opera, Via Lambro 38, I-20090 Opera (MI)).

The enzyme glutaryl-7-ACA acylase may be used in various forms, without this modifying its stereospecificity and its stereoselectivity. For example, glutaryl-7-ACA acylase may be used in soluble or else immobilized form. In this second case, the enzyme is generally immobilized in accordance with techniques which are well known to the person skilled in the art. For example, the enzyme may be contained in polymeric gels or else attached to solid supports by covalent bonding, crosslinking, adsorption or encapsulation. Appropriate supports which are commonly used are, for example, porous glass, porous ceramics, synthetic polymers (for example pulystyrene, polyvinyl alcohols, polyethylene, polyamides or polyacrylamides), or polymers of natural origin (for example cellulose).

Through the use of the enzyme glutaryl-7-ACA acylase it is possible to obtain for each enantiomer a high enantiomeric excess ("ee"), in particular greater than or equal to about 90%, or even greater than or equal to about 95%, and preferably greater than or equal to about 99%. In the context of the present invention, the "enantiomeric excess" refers to the % excess of one of the enantiomers relative to the racemic mixture. More specifically, the enantiomeric excess is calculated as follows:

$$ee(\%) = \frac{[R]-[S]}{[R]+[S]} *100 = \%(R) - \%(S)$$

where [R] and [S] represent the concentration of (R) and (S) enantiomer respectively.

Generally, the amount of enzymes employed relative to the total amount of initial amino acid (substrate) is between about 1 and 100 units (U) per mole of substrate, and preferably between about 10 and 40 units per mmole of substrate. 1 unit of enzyme corresponds to the amount of enzyme required to hydrolyse 1 Mmol of N-glutaryl-7-aminoacetoxycephalosporinic acid per minute under standard pH and temperature conditions which are known to the person skilled in the art.

According to the invention, the reaction is carried out in an optionally buffered aqueous medium. In this case, the aqueous buffer, with a concentration of between about 10 mM and 200 mM, may be selected from acetate buffers which can be used at a pH of between about 5 and 6.5, or phosphate buffers which can be used at a pH of between about 6.5 and 8, or else pyrophosphate buffers which can be used at a pH of between about 8 and 9.

The process of the invention is therefore implemented in a medium in which the pH is monitored and adjusted to between about 6 and 9. In one embodiment, the pH of the reaction medium is monitored and adjusted specifically to between about 7.5 and 8.5, and in another embodiment between about 8 and 8.5. The pH may be monitored with the aid of a pH-stat by the addition of an acid such as, for example, hydrochloric acid, sulphuric acid or phosphoric acid and a base such as, for example, sodium hydroxide, potassium hydroxide or aqueous ammonia.

The treatment of the amino acids in accordance with the invention with glutaric anhydride is implemented at a temperature of between about 20° C. and 40° C., and generally between about 25° C. and 35° C. Moreover, the second step, employing the enzyme glutaryl-7-ACA acylase, is carried out at a temperature of between about 10° C. and 50° C., and generally about 25° C. and 35° C.

Lastly, the reaction time varies comprehensively between about 1 hour and 100 hours and depends in particular on the amino acid concerned and on the enzyme concentration. Generally, the reaction is left to proceed for as long as is needed to obtain the desired enantiomer with a satisfactory enantiomeric excess. The amount of chiral amino acid obtained and the value of the enantiomeric excess are monitored using the conventional techniques known to the person skilled in the art. Advantageously, monitoring is carried out by means of HPLC (High Performance Liquid Chromatography).

According to the present invention, the (R) and (S) enantiomers obtained by the process described above may be separated easily, owing to the fact that one is present in the form of an amine which is soluble in an aqueous medium and the other is present in the form of a solid amide. Consequently, a further subject of the present invention relates to the process as set out above which comprises as a subsequent step the separation of the (R) and (S) enantiomers.

Figure 2:
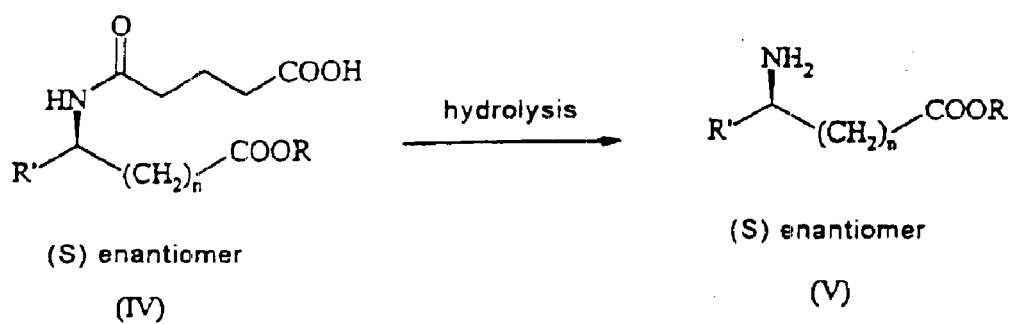
FIG. 2: Schematic representation of the step of transforming the chiral glutarylamide derivative into its corresponding chiral amino acid by hydrolysis.
Figure 2:
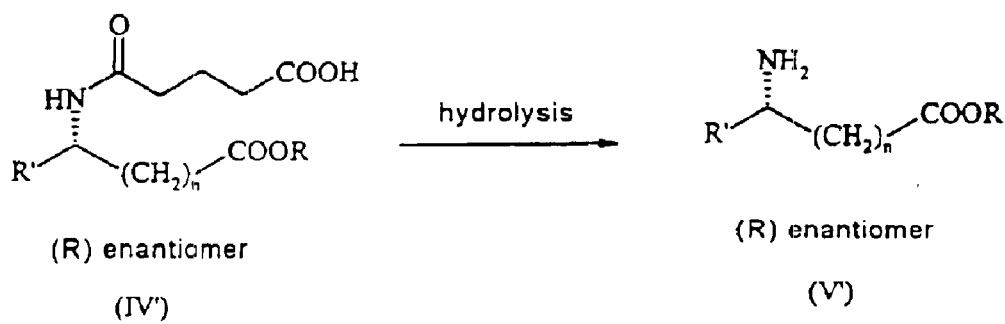

The separation of the said (R) and (S) enantiomers may be carried out easily by virtue of conventional techniques which are known to the person skilled in the art. This is done, for example, by filtration, extraction, chromatography or crystallization.

Where the desire is to isolate the other enantiomer in the amino acid form and not in the glutarylamide derivative form, the said enantiomer of the glutarylamide derivative which has been isolated in accordance with the process described above is then hydrolysed so as to recover the corresponding amino acid in the enantiomeric form. It should be noted that this process is advantageous since the hydrolysis allows the stereochemistry of the compound employed to be retained and does not lead to racemization of the chiral glutarylamide derivative. Where the amino acids are of general formula (I), this additional step may be represented by the reaction scheme according to FIG. 2.

The hydrolysis is carried out in accordance with conventional techniques which are known to the person skilled in the art. The hydrolysis in question may in particular be an acidic or a basic hydrolysis. In the latter case, it is carried out, for example, in the presence of a base such as sodium hydroxide, at a temperature between about 50° C. and 90° C. and under atmospheric pressure. However, any other operating conditions which are also suitable and known to the person skilled in the art may be used.

The present invention is useful in the sense that it allows amino acids in racemic form to be resolved, thereby making it possible to have available one or the other enantiomer of the said amino acid, the said enantiomers constituting, in particular, synthesis intermediates.

By way of illustration, the present invention makes it possible, for example, to have available (S)-3-amino-3-phenylpropanoic acid, which constitutes an intermediate in the synthesis of the compound of general formula:

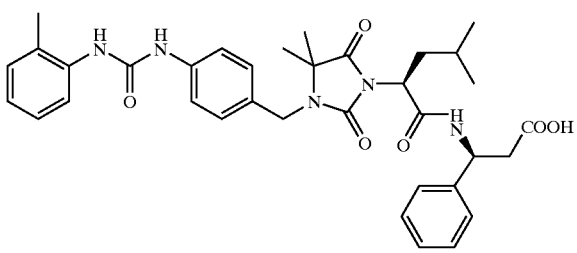

which is a VLA4 receptor antagonist involved in particular in asthmatic disorders.

As well as the preceding provisions, the present invention also embraces features and advantages which will emerge from the examples which follow, and which should be considered as illustrative of the invention without limiting its scope.

EXAMPLES

Example 1

Resolution of 3-amino-3-(4'-nitrophenyl)propanoic acid in the form of the racemic mixture a) Acylation of racemic 3-amino-3-(4'-nitrophenyl)propanoic acid 40.6 g of racemic 3-amino-3-(4'-nitrophenyl)propanoic acid were dissolved in 200 ml of distilled water and 55 ml of triethylamine. 29.4 g of glutaric anhydride were added in small portions and the reaction mixture was stirred for 1 hour. The reaction mixture was then acidified with 8.2 ml of 95% (weight/volume) sulphuric acid. The precipitate thus obtained was filtered off, washed 3 times with 15 ml of distilled water and dried to constant weight under vacuum at 55° C. This gave 52.84 g of racemic 3-(glutarylamide)-3-(4'-nitrophenyl)propanoic acid. The nature of the product obtained was determined by HPLC (High Performance Liquid Chromatography).

b) Enzymatic Deacylation Using Crystalline Glutaryl-7-ACA Acylase in Suspension (100 ml Reactor)

20 g of the acid obtained in the preceding step were dissolved in 75 ml of distilled water. The pH of the suspension was adjusted to 8.2 by adding 11.2 ml of 30% (weight/volume) sodium hydroxide. 826 mg (626 units) of a suspension of crystalline glutaryl-7-ACA acylase were added to this solution. The reaction mixture was stirred at 35° C. for 51 hours and at a pH which was monitored and adjusted to between 7.9 and 8.1. At the end of the reaction, the reaction mixture was cooled to 20° C. and the pH was adjusted to 7.0 by adding 5N hydrochloric acid. 20 ml of ethanol were then added. The resulting precipitate of (R)-3-amino-3-(4'-nitrophenyl)propanoic acid was filtered off, washed 3 times with 30 ml of ethanol, and dried to constant weight under vacuum at 45° C. This gave 5.65 g of (R)-3-amino-3-(4'-nitrophenyl)propanoic acid with an enantiomeric excess of greater than 99%.

The mother liquor was acidified with 17.5 ml of 5N hydrochloric acid. The precipitate which forms was filtered off and washed twice with 10 ml of distilled water. The filter cake obtained was dried to constant weight under vacuum at 45° C. This gave 8.25 g of (S)-3-(glutarylamide)-3-(4'-nitrophenyl)propanoic acid and (R)-3-(glutarylamide)-3-(4'-nitrophenyl)propanoic acid in a 91:9 ratio. The nature of the products obtained was determined by HPLC.

c) Enzymatic Deacylation Using Immobilized Glutaryl-7-ACA Acylase Obtained from Roche Diagnostic GmbH (100 ml Reactor)

20.5 g of the acid obtained in step a) were dissolved in 75 ml of distilled water. The pH of the suspension was adjusted to 8.2 by adding 11.9 ml of 30% (weight/volume) sodium hydroxide. 6.2 g (632.4 units) of moist immobilized glutaryl-7-ACA acylase (Roche Diagnostic GmbH) were added to this solution. The reaction mixture was stirred at 35° C. for 18 hours and at a pH which was monitored and adjusted to between 7.9 and 8.1. At the end of the reaction, the pH of the reaction mixture was adjusted to 9.5 by addition of 30% (weight/volume) sodium hydroxide and the volume of the reaction mixture was adjusted to 200 ml so as to dissolve the (R)-3-amino-3-(4'-nitrophenyl)propanoic acid produced. The immobilized enzyme was removed by filtration and the pH of the mother liquor was adjusted to 7.0 by addition of 5N hydrochloric acid. Then 50 ml of ethanol were added to the reaction mixture. The precipitated (R)-3-amino-3-(4'-nitrophenyl)propanoic acid was filtered off, washed with 10 ml of ethanol and dried to constant weight under vacuum at 45° C. This gave 5.375 g of (R)-3-amino-3-(4'-nitrophenyl)-propanoic acid with an enantiomeric excess equal to 98%.

The mother liquor was acidified with 20 ml of 5N hydrochloric acid. The precipitate which forms was filtered off and washed twice with 15 ml of distilled water. The filter cake was dried to constant weight under vacuum at 45° C. This gave 6 g of (S)-3-(glutarylamide)-3-(4'-nitrophenyl)propanoic acid in a 94:6 ratio.

The nature of the products obtained was determined by HPLC.

d) Enzymatic Deacylation Using Crystalline Glutaryl-7-ACA Acylase in Suspension (500 ml Reactor)

100 g of racemic 3-(glutarylamide)-3-(4'-nitrophenyl)propanoic acid obtained as in step a) were dissolved in 400 ml of distilled water. The pH of the suspension was adjusted to 8.2 by adding 60 ml of 30% (weight/volume) sodium hydroxide. 6.4 mg (4653 units) of a suspension of crystalline glutaryl-7-ACA acylase were added to this solution. The reaction mixture was stirred at 35° C. for 30 hours and at a pH which was monitored and adjusted to between 7.9 and 8.1. At the end of the reaction, the reaction mixture was cooled to 20° C. and the pH was adjusted to 13 by addition of 25 ml of 30% (weight/volume) sodium hydroxide so as to dissolve the (R)-3-amino-3-(4'-nitrophenyl)propanoic acid formed. The insoluble particles were filtered and the pH of the mother liquor was adjusted to 7.0 by addition of 27 ml of 36% hydrochloric acid. Then 100 ml of ethanol were added to the reaction mixture. The precipitate of (R)-3-amino-3-(4'-nitrophenyl)propanoic acid obtained was filtered off, washed twice with 100 ml of ethanol and dried to constant weight under vacuum at 45° C. This gave 28.87 g of (R)-3-amino-3-(4'-nitrophenyl)propanoic acid with an enantiomeric excess equal to 97%.

The nature of the product obtained was determined by HPLC.

Example 2

Resolution of 3-amino-3-phenylpropanoic acid in the form of the racemic mixture a) Acylation of racemic 3-amino-3-phenylpropanoic acid 488 g of racemic 3-amino-3-phenylpropanoic acid were dissolved in 2 liters of distilled water containing 236 g of sodium hydroxide in the form of pellets. 437.5 g of glutaric anhydride were added in small portions to the reaction mixture over 1 hour, with stirring and at 20° C. After 1 hour, the reaction mixture was acidified with 236 ml of 95% (weight/volume) sulphuric acid and cooled to 10° C. The precipitate thus formed was filtered and then washed 3 times with 600 ml of distilled water. The moist filter cake thus obtained, weighing 1610 g, contained 602 g of racemic 3-glutarylamide-3-phenylpropanoic acid. The nature of the products obtained was determined by HPLC.

b) Enzymatic Deacylation Using Crystalline Glutaryl-7-ACA Acylase in Suspension (5 Liter Reactor)

1575 g of the moist filter cake obtained before, containing 589 g of racemic 3-glutarylamide-3-phenylpropanoic acid, were dissolved in 1610 ml of distilled water. The pH of the suspension was adjusted to 8.0 by adding 440 ml of 30% (weight/volume) sodium hydroxide. 52.6 g (32,000 units) of a suspension of crystalline glutaryl-7-ACA acylase were added to this solution. The reaction mixture was stirred at 35° C. for 41 hours and at a pH which was monitored and adjusted to between 7.9 and 8.1. At the end of the reaction, the reaction mixture was cooled to 20° C. and the pH was adjusted to 13 by addition of 25 ml of 30% (weight/volume) sodium hydroxide so as to dissolve the (R)-3-amino-3-(4'-nitrophenyl)propanoic acid produced. The insoluble particles were filtered off and the pH of the mother liquor was adjusted to 7.0 by addition of 27 ml of 36% hydrochloric acid.

The resulting precipitate of (R)-3-amino-3-phenylpropanoic acid was filtered off, washed with 150 ml of distilled water and dried to constant weight under vacuum at 45° C. This gave 96.9 g of (R)-3-amino-3-phenylpropanoic acid with an enantiomeric excess equal to 98%.

The mother liquor was acidified with 180 ml of 95% (weight/volume) sulphuric acid. The precipitate thus formed was filtered off and washed twice with 400 ml of cooled distilled water. The filter cake was dried to constant weight under vacuum at 45° C. This gave 314.6 g of (S)-3-(glutarylamide)-3-phenylpropanoic acid and (R)-3-(glutarylamide)-3-phenylpropanoic acid in a 90:10 ratio.

The nature of the products obtained was determined by HPLC.

c) Deacylation of (S)-3-glutarylamide-3-phenylpropanoic acid by basic hydrolysis 557.2 g of a mixture of (S)-3-glutarylamide-3-phenylpropanoic acid and (R)-3-glutarylamide-3-phenylpropanoic acid in a 90:10 ratio, obtained in preceding step b), were distilled in 3.91 liters of distilled water and 1.65 liters of 30% (weight/volume) sodium hydroxide. The reaction mixture was stirred at 70° C. for 4 days.

The reaction mixture was then cooled to 15° C. The product obtained was precipitated with adjustment of the pH to 6.9 by addition of 3.21 liters of 37% (weight/volume) hydrochloric acid, filtered off, and dried to constant weight under vacuum at 45° C. This gave 202.4 g of (S)-3-amino-3-phenylpropanoic acid and (R)-3-amino-3-phenylpropanoic acid with an enantiomeric excess of greater than 98%.

The nature of the products obtained was determined by HPLC.

What is claimed is:

1. A process for separating the enantiomers of an amino acid, comprising:
   treating a racemic mixture of the amino acid with glutaric anhydride to form glutarylamide compounds of the enantiomers; and
   treating the glutarylamide compounds of the enantiomers with glutaryl-7-ACA acylase to recover one of the enantiomers of the amino acid, the other enantiomer remaining in the form of a glutarylamide compound.

2. The process of claim 1, wherein the amino acid has the formula (I):

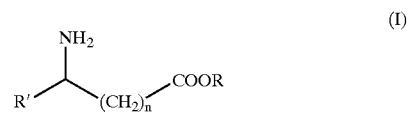

in which
   n is an integer chosen from 0, 1, 2, 3, 4, 5, and 6,
   R represents a hydrogen atom or an optionally substituted radical chosen from alkyl, alkene, alkyne, cycloalkyl, aryl, condensed polycyclic hydrocarbon, and heterocycle,
   and R' represents an optionally substituted radical chosen from alkyl, alkene, alkyne, cycloalkyl, aryl, condensed polycyclic hydrocarbon, and heterocycle, or an oxy, thio, sulphoxide or sulphonyl radical substituted by an optionally substituted radical chosen from alkyl, aryl, cycloalkyl, and heterocycle.

3. The process of claim 2, wherein n is an integer chosen from 0, 1, 2, and 3, and R represents a hydrogen atom, an alkyl radical, or an aryl radical.

4. The process of claim 2, wherein n is an integer equal to 0, 1 or 2, R represents a hydrogen atom or an alkyl radical, and R' is chosen from optionally substituted heterocycles and aryls.

5. The process of claim 1, wherein the glutaryl-7-ACA acylase is in soluble form.

6. The process of claim 1, wherein the glutaryl-7-ACA acylase is in immobilized form.

7. The process of claim 1, wherein an amount of enzyme employed relative to a total amount of initial amino acid substrate is between about 1 and 100 units per mmole of the initial amino acid substrate.

8. The process of claim 2, wherein an amount of enzyme employed relative to a total amount of initial amino acid substrate is between about 1 and 100 units per mmole of the initial amino acid substrate.

9. The process of claim 1, wherein the treatment is carried out in a buffered aqueous medium.

10. The process of claim 9, wherein the buffered aqueous medium comprises an aqueous buffer having a concentration of between about 10 mM and 200 mM and is chosen from acetate buffers that are used at a pH of between about 5 and 6.5, phosphate buffers that are used at a pH of between about 6.5 and 8, and pyrophosphate buffers that are used at a pH of between about 8 and 9.

11. The process of claim 1, wherein the racemic mixture has a pH that is monitored and adjusted to between about 6 and 9.

12. The process of claim 1, wherein the treatment of the amino acid with glutaric anhydride occurs at a temperature of between about 20° C. and 40° C.

13. The process of claim 1, wherein the treatment with the glutaryl-7-ACA acylase occurs at a temperature of between about 10° C. and 50° C.

14. The process of claim 1, wherein the treating lasts between about 1 hour and 100 hours.

15. The process of claim 1, further comprising separating (R) and (S) enantiomers.

16. The process of claim 15, wherein the separation of the (R) and (S) enantiomers is carried out by filtration, extraction, chromatography, or crystallization.

17. The process of claim 15, wherein the separated enantiomer remaining in the form of the glutarylamide compound is hydrolyzed so as to recover the corresponding amino acid in enantiomeric form.

18. The process of claim 16, wherein the separated enantiomer remaining in the form of the glutarylamide compound is hydrolyzed so as to recover the corresponding amino acid in enantiomeric form.

19. A process for separating enantiomers of an amino acid, comprising:
  treating a racemic mixture of the amino acid with glutaric anhydride to form glutarylamide compounds of the enantiomers;
  treating the glutarylamide compounds of the enantiomers with glutaryl-7-ACA acylase to recover one of the enantiomers of the amino acid, the other enantiomer remaining in the form of a glutarylamide compound; and
  then separating the two enantiomers.

20. A process for separating enantiomers of an amino acid, comprising:
  treating a racemic mixture of the amino acid with glutaric anhydride to form glutarylamide compounds of the enantiomers;
  treating the glutarylamide compounds of the enantiomers with glutaryl-7-ACA acylase to recover one of the enantiomers of the amino acid, the other enantiomer remaining in the form of a glutarylamide compound;
  then separating the two enantiomers; and
  hydrolyzing the enantiomer remaining in the form of the glutarylamide compound so as to recover the corresponding amino acid in enantiomeric form.

* * * * *